United States Patent [19]

Barton et al.

[11] 4,234,515

[45] Nov. 18, 1980

[54] PREPARATION OF N,N-DIFLUOROAMINES

[75] Inventors: Derek H. R. Barton, London, England; Robert H. Hesse, Cambridge, Mass.

[73] Assignee: Research Institute for Medicine & Chemistry Inc., Cambridge, Mass.

[21] Appl. No.: 904,338

[22] Filed: May 9, 1978

Related U.S. Application Data

[63] Continuation of Ser. No. 591,762, Jun. 30, 1975, abandoned, which is a continuation of Ser. No. 373,732, Jun. 26, 1973, abandoned.

[30] Foreign Application Priority Data

Jun. 27, 1972 [GB] United Kingdom ............... 30128/72

[51] Int. Cl.$^3$ .............................................. C07C 85/18
[52] U.S. Cl. ................................. 564/114; 260/453 P; 260/694; 560/8; 560/129; 562/405; 562/412
[58] Field of Search ................. 260/570.8 R, 583 NH, 260/563 R, 578

[56] References Cited

U.S. PATENT DOCUMENTS

| 3,324,181 | 6/1967 | Dineen et al. ................ 260/583 NH |
| 3,714,215 | 1/1973 | d'Ostyrowick et al. ......... 260/453 R |
| 3,751,473 | 8/1973 | Hill et al. ............................. 260/577 |

OTHER PUBLICATIONS

Merritt et al., "J. Org. Chem.", vol. 32, pp. 416-419 (1967).
Moldavskii et al., "Chem. Ab.", vol 74, Abstract No. 99375p (1971).
Sidgwick, "The Organic Chemistry of Nitrogen", pp. 243 & 450 (1966).
Hesse et al., "Chem. Ab.", vol. 76, Ab. No. 72474z (1972).
Fieser et al., "Reagents for Organic Synthesis", vol. 4, p. 37 (1974).

Primary Examiner—John Doll
Attorney, Agent, or Firm—Bacon & Thomas

[57] ABSTRACT

N,N-difluoroamines are prepared by fluorination of compounds containing a >C=N— bond using molecular fluorine or a hypofluorite in which the fluoroxy group is bonded to an inert electron attracting group, such hypofluorites including fluoroalkyl hypofluorites such as trifluoromethyl hypofluorite. The fluorination is advantageously conducted in the presence of an alkanol or other nucleophilic compound. Suitable starting materials include imino ethers and esters and aliphatic and aromatic Schiff's bases, use of the latter being particularly convenient.

20 Claims, No Drawings

PREPARATION OF N,N-DIFLUOROAMINES

This is a continuation of application Ser. No. 591,762, filed June 30, 1975 now abandoned, which is in turn a continuation of application Ser. No. 373,732, filed June 26, 1973, now abandoned.

This invention relates to a process for the preparation of N-fluorinated organic nitrogen compounds, more particularly to the preparation of N,N-difluoroamino compounds.

The preparation of N-fluorinated organic nitrogen compounds, for example compounds containing an N-monofluoroamino or N,N-difluoroamino group is of considerable interest in, for example, the study of biologically active systems. Thus it is known that the substitution of a fluorine atom for a hydrogen atom in certain biologically active molecules can significantly alter the activity of the compound; the activity of 9α-fluorocortisol 21-acetate, for example, exceeds that of cortisol 21-acetate about ten-fold. In the field of biologically active amine derivatives there is evidence that replacement of, for example, primary amine groups by difluoroamino groups leads to compounds having improved properties as regards, inter alia, resistance to biological oxidation and other deactivation reactions.

A number of processes are known for the introduction of an $-NF_2$ group into organic compounds, for example the addition of $NF_2$ radicals to unsaturated linkages, the alkylation of $HNF_2$, and the cleavage of carboxamides and N-alkyl carbamates with elemental fluorine. These reactions suffer a number of disadvantages, however, which render them unsuitable as general methods for the introduction of $-NF_2$ groups, particularly where sensitive or complex substrates such as bio-active molecules are used. Thus the reactions generally lack selectivity and tend to give unwanted side products, particularly in the case of reaction with elemental fluorine, which tends to be excessively vigorous. Addition of $NF_2$ radicals suffers the disadvantage that the reaction tends to be sluggish and thus requires high temperatures, while the use of $HNF_2$ requires strongly acidic conditions and is limited to attachment of the fluorinated amino group at a potentially highly electrophilic carbon atom. Furthermore, the reagents such as difluoramine and tetrafluorohydrazine used in these processes are extremely hazardous to handle.

We have now found that a variety of compounds, including sensitive biologically active molecules, containing an $-NF_2$ group may be prepared under mild conditions and with good yield and selectivity by reaction of a range of imino derivatives with certain electrophilic fluorinating agents.

Thus we provide a process for the preparation of an N,N-difluoroamine of general formula $$R-NF_2 \qquad (I)$$

(where R represents a hydrogen atom or an organic group) wherein a compound of general formula

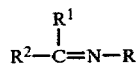

(where R is as defined for formula I, $R^1$ represents an organic group and $R^2$ represents a hydrogen atom or an organic group, two or more of R, $R^1$ and $R^2$ if desired, being joined in divalent or trivalent groupings forming cyclic structures) is reacted with a fluorinating agent comprising elemental fluorine or a hypofluorite in which the fluoroxy group is bonded to an inert electron attracting group.

As is explained in detail hereinafter, it is preferred that the reaction should be carried out under mild conditions to avoid attack by the fluorinating agent at other centres of the molecule. This is particularly relevant when using elemental fluorine. Consequently it is preferred to select conditions which facilitate the reaction and we have found that the reaction proceeds more readily in the presence of a nucleophile or when $R^1$ and/or $R^2$ are able to release electrons. Furthermore, the addition of elemental fluorine is preferably controlled by diluting the fluorine with an inert gas before reaction and/or introducing the fluorine into the reaction system at reduced pressure.

Any ethylenic or acetylenic multiple bonds in the groups R, $R^1$ and $R^2$ will tend to be fluorinated under the reaction conditions employed unless such bonds are deactivated by being substituted with or conjugated with electron withdrawing groups. Thus it is generally preferred that the groups R, $R^1$ and $R^2$ do not contain ethylenic or acetylenic bonds unless these are deactivated as described above or unless additional fluorination is desired in a particular case. Apart from this restriction, however, a broad range of compounds of formula II may be used.

As indicated above, compounds of formula II in which one or both of the groups $R^1$ and $R^2$ are able to release electrons are conveniently used in the process. Useful compounds of this type include imino ethers and esters, i.e. compounds in which one of $R^1$ and $R^2$ is a C-linked organic group and the other is an O-linked organic group, particularly compounds of general formula

where $R^a$, $R^b$ and R are hydrocarbyl groups ($R^b$ being an etherifying or esterifying group), said groups preferably being selected from aliphatic, cycloaliphatic, araliphatic and aromatic groups.

Other useful compounds of formula II of the above type are those in which one of the groups is an electron releasing aryl group, i.e. an aromatic ring carrying one or more appropriately positioned electron releasing substituents, such compounds comprising Schiff's bases derived from an amine $RNH_2$ (where R is as defined for formula I) and an appropriately substituted aromatic aldehyde or ketone. Preferred compounds within this class are those of formula

where R is as defined for formula III, $R^c$ is a hydrogen atom or a hydrocarbyl group, preferably an aliphatic, cycloaliphatic, araliphatic or aromatic group, and $R^d$ is an aromatic ring carrying one or more appropriately positioned electron releasing substituents. The substituents present in the group $R^d$ are preferably inert to the reaction conditions employed, and thus suitable groups $R^d$ include carbocyclic aromatic rings such as phenyl substituted in the ortho- and/or para- positions by, for example, one or more groups selected from alkoxy, preferably containing 1-6 carbon atoms, e.g. methoxy, ethoxy, n-propoxy, isopropoxy, t-butoxy; aralkoxy, preferably containing 1-6 carbon atoms in the alkyl group, e.g. benzyloxy; aryloxy e.g. phenoxy; sulphur analogues of the above oxygen functions; and dialkylamino, wherein the alkyl groups preferably contain 1-6 carbon atoms, e.g. dimethylamino, diethylamino.

Alternatively, as indicated above, the process may conveniently be carried out in the presence of a nucleophilic compound. Suitable compounds for this purpose include, for example, oxygen nucleophiles such as alcohols or salts of organic carboxylic acids, which serve as hereinafter described to introduce an electron releasing oxygen function into the molecule. Lower alkanols, e.g. containing 1-6 carbon atoms, such as methanol and ethanol are particularly convenient nucleophiles. Where the reaction is effected in the presence of such a nucleophile, compounds of formula II in which neither of the groups $R^1$ and $R^2$ possess electron releasing properties can be readily fluorinated, so that a wide range of compounds of formula II may be reacted in this manner. Preferred substrates of formula II for such reaction conditions include the Schiff's bases of formula

(V)

where R and $R^a$ are as defined for formula III and $R^c$ is as defined for formula IV.

In the above formulae III, IV and V the groups R, $R^a$, $R^b$ and $R^c$ may be, for example, alkyl groups containing 1-30, preferably 1-20 carbon atoms, e.g. methyl, ethyl, propyl, butyl, hexyl, decyl, pentadecyl, heptadecyl, octadecyl, eicosyl; cycloaliphatic groups containing 3-30, preferably 5-20 carbon atoms, e.g monocyclic or polycyclic (including bridged) cycloalkyl groups such as cyclopentyl, cyclohexyl, adamantyl and norbornyl, heteroatom-containing cyclic groups such as sugar groups, e.g allose or glucose groups and polycyclic groups such as steroidal groups; aralkyl groups containing 1-10, preferably 1-6 carbon atoms in the alkyl chain, e.g. benzyl, phenethyl, phenylpropyl or phenylisopropyl; aryl groups such as phenyl and naphthyl; and the above groups substituted by for example, oxo, nitro, cyano, halo such as fluoro or chloro, carboxy, hydroxy, esterified hydroxy e.g. lower alkylcarbonyloxy such as acetoxy or propionoxy or aralkylcarbonyloxy such as benzoyloxy, sulphonyl e.g. arylsulphonyl such as benzenesulphonyl, lower alkoxy such as methoxy or ethoxy, aralkoxy such as benzyloxy, or aryloxy such as phenoxy. It will be appreciated that when $R^b$ is an esterifying group, it will be a hydrocarbyl group possessing an oxo substituent in the 1-position.

Hypofluorites which may be used as fluorinating agent in the process include lower (e.g. $C_{1-6}$) fluoralkyl hypofluorites, the alkyl group preferably carrying at least 2 fluorine atoms per carbon atom. Preferred reagents of this type include trifluoromethyl, perfluoropropyl, perfluoroisopropyl, perfluoro-t-butyl, monochlorohexafluoropropyl and perfluoro-t-pentyl hypofluorites, 1,2-difluoroxytetrafluoroethane and difluoroxydifluoromethane. Inorgnic hypofluorites such as fluoroxysulphur pentafluoride may also be used. The use of trifluoromethyl hypofluorite is particularly preferred by virtue of its good selectivity and comparative ease of handling.

Where the hypofluorite is a gas or volatile liquid, it may conveniently be passed into the reaction mixture in gaseous form, if desired after mixing with a gaseous diluent such as nitrogen. Alternatively the hypofluorite may be dissolved in a solvent, advantageously a polar organic solvent, for example a halogenated hydrocarbon such as methylene dichloride, chloroform, chlorotrifluoromethane or a mixture of such hydrocarbons, a ketone such as acetone, an aliphatic ether such as diethyl ether or a cyclic ether such as tetrahydrofuran.

The reaction temperature is preferably kept relatively low, for example in the range $-78°$ to $+40°$ C. Reaction at room temperature with hypofluorites such as trifluoromethyl hypofluorite proceeds rapidly and smoothly.

Where elemental fluorine is used as the fluorinating agent, the gas is preferably either diluted with an inert gas such as nitrogen or argon, the concentration of fluorine in the gas being preferably 1 to 50% by volume, or added to the reaction system undiluted but at reduced pressure, e.g. less than 100 mm Hg in order to moderate the reaction and facilitate control. In general lower reaction temperatures will be used than those optimal for hypofluorite reagents, but the reaction is controllable at room temperature.

In order to produce an N,N-difluoroamine of formula I it is necessary for the appropriate compond of formula II to react with at least two equivalents of the fluorinating agent. While we do not wish to be bound by theoretical considerations it is believed that reaction of the compound (II) with one equivalent of fluorinating agent promotes electrophilic monofluorination of the nitrogen atom together with fission of the imine double bond, leading to formation of an intermediate carbonium ion of structure

(VI)

where R, $R^1$ and $R^2$ are as defined for formula II. This intermediate may then combine with a negative species present in the reaction system, for example a fluoride ion or an ion $R^FO^\ominus$ derived from a hypofluorite of formula $R^FOF$ to yield a neutral intermediate. Alternatively, a nucleophile present in the reaction system may react

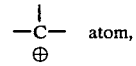 atom, in this case introducing an electron releasing substitutent into the molecule. The neutral intermediate so obtained may then react with a further equivalent of the fluorinating agent to introduce a second fluorine atom at the nitrogen atom, thus yielding a difluoroammonium derivative which subsequently decomposes with fission of the C—N bond to give the desired N,N-difluoroamine of formula I. Where a gaseous fluorinating reagent is used, a break in uptake of the gas can usually be observed during the reaction, indicating that the initial fluorination is largely complete before the final fluorinolysis stage takes place. This is confirmed by n.m.r.

examination of the medium during the course of the reaction.

Various subsidiary reactions may occur in certain cases, particularly where $R^2$ in formula II is a hydrogen atom. Thus, for example, HF may be eliminated from one of the intermediate structures to regenerate the imine double bond, which is then subjected to further fluorination and addition of negative species or nucleophilic attack. In most cases, however, such subsidiary reactions will ultimately yield the desired N,N-difluoroamine.

It is believed that the presence of an electron releasing group enhances the yield of N,N-difluoroamine by its effect on the decomposition of the N,N-difluoroammonium intermediate. As indicated above, this intermediate decomposes with fission of the C—N bond to yield the desired compound of formula I; it will be evident, however, that such an intermediate may also decompose with fission of the R—N bond to yield products such as compounds of formulae $RF$ and $R^1R^2R^xC.NF_2$ where R, $R^1$ and $R^2$ are as defined for formula II and $R^x$ is derived from a negative species such as fluoride ion or an ion $R^FO^\ominus$ derived from a hypofluorite $R^FOF$. The electron releasing group serves to enhance the electron density about the C—N bond, so that decomposition of the N,N-difluoroammonium derivative preferentially proceeds with C—N bond fission following electron capture by the nitrogen atom. By facilitating the above reaction, the electron releasing group permits the fluorination to proceed under very mild conditions and so enables side-reactions such as fluorination at other centres to be reduced or avoided.

Where one of the groups $R^1$ and $R^2$ is an electron releasing group, e.g. where $R^1$ or $R^2$ is a group $OR^b$ (where $R^b$ is as defined for formula III) or an electron donating aryl group, then this group will act directly on the C-N bond in the desired manner. Where a nucleophile such as an alcohol is present in the reaction medium this may react as described above with the intermediate carbonium ion of formula VI to yield a neutral intermediate of formula $$\begin{array}{c} R^1 \;\; F \\ | \;\; | \\ R^2-C-N-R \\ | \\ R^y \end{array} \qquad (VII)$$

where R, $R^1$ and $R^2$ are as defined for formula II and $R^y$ is the electron releasing residue of the nucleophile. The electron releasing group so introduced will thus have the desired influence on the C—N bond in the subsequent reactions to form the compound of formula I.

The N-monofluorinated intermediates are generally unstable and cannot normally be isolated. The compounds of formula II thus react virtually directly with 2 equivalents of the fluorinating agent to yield the desired compound of formula I. However, the N-monofluoro intermediates may be cleaved hydrolytically without isolation to yield an N-monofluoroamine of formula RNHF, for example by treatment with aqueous acid such as sulphuric, perchloric or methane sulphonic acid, after reaction of the compound of formula II with a single equivalent of fluorinating agent.

The starting materials of formula II used in the present process may readily be derived from, for example, a primary amine $RNH_2$ corresponding to the desired fluorinated amine of formula I. Thus such a primary amine may be reacted with an aldehyde or ketone under acidic or basic conditions to yield a Schiff's base of formula IV or V. Imino ethers of formula III may be prepared by, for example, reaction of the amine $RNH_2$ with an orthoester or by reaction of an amide formed from the amine, e.g. by reaction with an acylating agent such as an acyl halide, with an alkylating agent such as a trialkyl oxonium salt, an alkyl fluorosulphonate or a carbenium salt.

In many cases the aldehyde or ketone used or the acid or an acid derivative (e.g. an ester) corresponding to the acylating agent or orthoester used may be regenerated by hydrolytic work-up of the fluorination products and may thus be re-used with consequent saving in costs. This recycling of compounds corresponding to the moiety

in formula II may in certain instances be facilitated if one or both of the groups $R^1$ and $R^2$ is substituted with an acidic group, e.g. a carboxy group, so that the regenerated material may readily be isolated from the reaction solution by precipitation with strong acid, for example a mineral acid such as hydrochloric acid. One convenient class of fluorination substrates for this reason comprises Schiff's bases derived from amines of formula $RNH_2$ and p-carboxybenzaldehyde, since p-carboxybenzaldehyde can be recovered from the fluorination system by acidification whereby hydrolysis of initially formed carbonyl-derivatives is effected to regenerate the aldehyde group and the insoluble free acid is simultaneously precipitated. Where imines derived from compounds such as p-carboxybenzaldehyde are to be fluorinated we prefer to prepare the imine in situ under mildly basic condtions and effect its fluorination directly, since isolation of the acid sensitive imine carboxylate salt may give rise to difficulties.

The process of the invention thus provides a convenient and selective synthetic method for the preparation of a wide range of organic compounds containing N,N-difluoroamino groups, such compounds including, for example, steroids, alkaloids, amino sugars, amino saccharides, antibiotics and surfactants, using easily handled reagents. As indicated above, the ability to fluorinate amino groups present in biologically active amine derivatives is of advantage in that such fluorination may result in the improvement of properties such as resistance to biological oxidation and other deactivation reactions. Furthermore, the lipid-solubility of biologically active amines is enhanced by such fluorination, leading to greater penetration of lipid membranes on administration and in some cases resulting in greater duration of activity. Sugar amines can also with advantage be N,N-difluorinated and may, for example, be incorporated into physiologically active substances such as antibiotics. Useful compounds which have been prepared by the process of the invention include 1-difluoroaminoadamantane, which is toxic to Herpes virus, the (+)- and (−)-difluoroamphetamines, which are CNS active agents, and 2,4-dinitro-N,N-difluoroaniline, which is used as an additive in rocket fuels and explosives.

As indicated above, the invention also provides a process for the preparation of N-monofluoroamines of formula RNHF (where R is as defined for formula I) wherein the reaction of the compound of formula II with the fluorinating agent is curtailed after consumption of about one equivalent of fluorinating agent, and the reaction product is hydrolysed to yield the desired N-monofluoroamine, or a salt thereof.

The following non-limitative examples serve to illustrate the invention. All temperatures are in °C.

EXAMPLE 1

1-Difluoroaminoadamantane (a) Fluorination using CF$_3$OF

A solution of trifluoromethyl hypofluorite in trichlorofluoromethane was prepared by bubbling the hypofluorite through the solvent at −78°. α-Adamant-1-ylimino-α-ethoxy-p-fluorotoluene (300 mg., 1 mmole) in a mixture of chloroform (6 c.c.) and trichlorofluoromethane (2 c.c.) was treated with 2 mmoles of the dissolved hypofluorite for three hours at −78°, the reaction being monitored by gas layer chromatography. It was found that the first equivalent of hypofluorite was consumed within about 15 minutes, although some starting material was still present at this time, the second equivalent of hypofluorite reacting over the remainder of the three hours.

$^{19}$F n.m.r. examination of the system after the initial 15 minute reaction included signals at $\phi^* + 112.2$ (1F, m, atomatic fluorine),

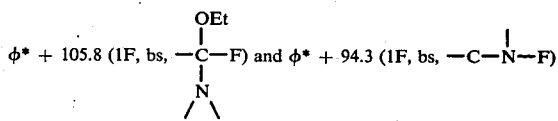

corresponding to the formation of N-adamant-1-yl-N-fluoro-α-ethoxy-α-fluoro-p-fluorobenzylamine as an intermediate.

After the three hour reaction at −78° the solution was warmed to room temperature and diluted with chloroform (20 c.c.). The resulting solution was washed with ice-cold aqueous sodium bicarbonate and with water and was dried over magnesium sulphate. The solvent was distilled off and the residue chromatographed on an alumina column using n-hexane as eluant to give 1-difluoroaminoadamantane (130 mg, 70%). After sublimation at 100° and 20 mm. Hg pressure the product had m.p. 113°–115° (sealed tube); $^1$H n.m.r. signals (CDCl$_3$) at δ 1.7–2.1 (1-adamantyl protons); $^{19}$F n.m.r. signal (CDCl$_3$) at $\phi^* -20.3$ (bs, —NF$_2$).

$^{19}$F n.m.r. examination of the reaction system also indicated the presence of α-ethoxy-α,α-difluoro-p-fluorotoluene

[$\phi^* + 110.4$ (1F, m, aromatic fluorine) and $\phi^* + 68.8$ (2F, s, —CF$_2$—OEt)]

in the reaction product, this compound rapidly being converted to ethyl p-fluorobenzoate on exposure to moisture and being eluted from the alumina column as the p-fluorobenzoate by addition of further n-hexane.

(b) Fluorination using SF$_5$OF

Fluoroxysulphur pentafluoride (2 mmole) was condensed in a flask cooled with liquid nitrogen and containing trichlorofluoromethane (50 c.c.). The flask was then warmed to −78° and α-adamant-1-ylimino-α-ethoxy-p-fluorotoluene (300 mg., 1 mmole) in a mixture of chloroform (6 c.c.) and trichlorofluoromethane (2 c.c.) was added. The resulting mixture was gently stirred and slowly warmed to room temperature until all the fluoroxy reagent was consumed (as evidenced by gas layer chromatography). Work up as in Example 1(a) gave 1-difluoroaminoadamantane (100 mg., 54%) identical to the product of Example 1(a).

(c) Fluorination with CF$_2$(OF)$_2$

The method of Example 1(b) was used except that 1 mmole (i.e. 2 milliequivalents) of difluoroxydifluoromethane were used in place of the fluoroxysulphur pentafluoride. Work up as in Example 1(a) gave 1-difluoroaminoadamantane (106 mg., 57%) identical to the product of Example 1(a).

(d) Fluorination with molecular fluorine

α-Adamant-1-ylimino-α-ethoxy-p-fluorotoluene (300 mg., 1 mmole) in a mixture of chloroform (6 c.c.) and trichlorofluoromethane (2 c.c.) was treated with a stream of nitrogen containing molecular fluorine (N$_2$:F$_2$ ~ 5:1) at −78°, the reaction being monitored by gas layer chromatography. Work up as in Example 1(a) gave 1-difluoroaminoadamantane (100 mg., 54%) identical to the product of Example 1(a).

EXAMPLE 2

(+)- and (−)-1-Phenyl-2-difluoroaminopropane (−)-α-(1-Phenylprop-2-ylimino)-α-ethoxytoluene (2.6 g., 10 mmoles) and calcium oxide (2.6 g.) in trichlorofluoromethane (50 c.c.) at −78° were treated with trifluoromethyl hypofluorite gas (2 mmoles) diluted with an approximately equal volume of nitrogen.

The gaseous fluorinating agent was added over about 30 minutes, after which the solution was stirred for a further 3 hours. The calcium oxide was then filtered off and the solvent evaporated to give a liquid residue. Column chromatography of this residue using alumina and eluting with n-hexane afforded (+)-1-phenyl-2-difluoroaminopropane (1.44 g., 84%); b.p. 91°–92°/20 mm. Hg; n$_D^{22°}$=1.4745; α$_D^{23°}$=+5° (c=111.6 mg/c.c.); $^1$H n.m.r. (CCl$_4$) signals at δ 1.2 (3H, slightly broadened doublet,

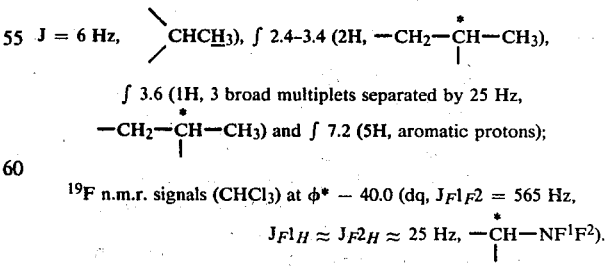

∫ 3.6 (1H, 3 broad multiplets separated by 25 Hz,

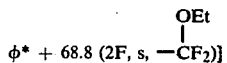

—CH$_2$—CH—CH$_3$) and ∫ 7.2 (5H, aromatic protons);

$^{19}$F n.m.r. signals (CHCl$_3$) at $\phi^* -40.0$ (dq, J$_{F^1F^2}$ = 565 Hz, J$_{F^1H}$ ≈ J$_{F^2H}$ ≈ 25 Hz, —CH—NF$^1$F$^2$).

Similar reaction of (+)-α-(1-phenylprop-2-ylimino)-α-ethoxy-p-fluorotoluene (2.05 g., 7.2 mmoles) together with calcium oxide (2.05 g.) and trichlorofluoromethane (50 c.c.) at −78° afforded (−)-1-phenyl-2-difluoroaminopropane (1.2 g., 75%); $N_D^{22°}=1.4745$; $\alpha_D^{25°}=-5°$ (c=20.1 mg./c.c.); the product had identical $^1H$ and $^{19}F$ n.m.r. spectra to the (+)-isomer.

EXAMPLE 3

N,N-Difluorostearamine

Trifluoromethyl hypofluorite gas (7 mmoles) diluted with an approximately equal volume of nitrogen was bubbled into a solution of α-ethoxy-α-stearyliminotoluene (1.3 g., 3.4 mmoles) in a 1:1 mixture of chloroform and trichlorofluoromethane (80 c.c.) at −78°, the solution further containing 1.5 g. of calcium oxide. After completion of the reaction as evidenced by gas layer chromatography the calcium oxide was filtered off and the resulting solution washed with ice-cold aqueous sodium bicarbonate and with water, and was dried over magnesium sulphate. The solvent was distilled off and the liquid residue chromatographed on a silica gel column eluting with n-hexane to yield N,N-difluorostearamine (0.54 g., 52%); $^1H$ n.m.r. signals at δ 0.8–1.3 (35H, $CH_3—(CH_2)_{16}—$), δ 3.4 (2H, tt, J=29 Hz and 7 Hz, $—CH_2C\underline{H}_2NF_2$); $^{19}F$ n.m.r. signals at $\phi*-55.6$ (2F, t, J=29 Hz, $—CH_2NF_2$). (Found: C 70.64; H 12.05; N 4.47. $C_{18}H_{13}NF_2$ requires C 70.77; H 12.21; N 4.59%).

EXAMPLE 4

(i) N,N-Difluoro-O-benzoyltyramine

O,N-Dibenzoyltyramine (2 g., 5.8 mmoles) and triethyloxonium fluoroborate in dry methylene chloride (55 c.c.) was kept at room temperature overnight. The solution was washed with ice-cold aqueous sodium carbonate and with water, and was then dried over magnesium sulphate. Removal of the solvent gave 2.48 g. residue containing α-ethoxy-α-(O-benzoyltyrimino)-toluene as evidenced by $^1H$ n.m.r. signals (CDCl$_3$) at δ 1.3 (3H, t, J=7 Hz, $—OCH_2C\underline{H}_3$), δ 2.9 (2H), δ 3.6 (2H), δ 4.2 (2H, q, J=7 Hz, $—OC\underline{H}_2CH_3$) and δ 7.3–8.1 (14H, aromatic protons). The crude product is chloroform at −50° C. was fluorinated by introduction of trifluoromethyl hypofluorite gas (2 equivalents) diluted with nitrogen. After three hours at −50° C. the reaction mixture was warmed to room temperature. The products were chromatographed on a silica gel column. Elution with n-hexane gave N,N-difluoro-O-benzoyltyramine, (500 mg., 1.8 mmole) which was purified by crystallization from n-hexane. The crystallised product had m.p. 67°–67.5°; $^1H$ n.m.r. signals (CDCl$_3$) at δ 3.0 (2H, t, J=7 Hz, Ar—$C\underline{H}_2CH_2—$), δ 3.6 (2H, tt, $J_{HH}=7$ Hz, $J_{HF}=28$ Hz, $—CH_2C\underline{H}_2NF_2$), δ 7.0, 7.4, 8.1 (Total 9H, aromatic protons); $^{19}F$ n.m.r. signals (CDCl$_3$) at $\phi*-54.8$ (t, J=28 Hz, $—CH_2NF_2$).

Successive elution with 5% methanol in chloroform afforded unreacted O,N-dibenzoyltyramine (0.8 g., 2.3 mmoles). The yield of N,N-difluoro-O-benzoyltyramine based on recovered starting material was 50%.

(ii) N,N-Difluorotyramine

N,N-Difluoro-O-benzoyltyramine (130 mg.) in methanol saturated with HCl was heated at 60° C. for 3 hours. The title compound (40 mg, 40%), isolated by preparative layer chromatography on silica gel, was a liquid at room temperature, and exhibited $^1H$ n.m.r. signals, (CDCl$_3$) at δ 3.0 (2H, t, J=8 Hz, Ar—$C\underline{H}_2—CH_2—$), δ 3.6 (2H, tt, $J_{HH}=8$ Hz, $J_{HF}=27$ Hz, $—CH_2C\underline{H}_2NF_2$), δ 4.9 (1H, bs, exchangeable with D$_2$O, $—OH$) and δ 6.8 (4H, m, aromatic protons); $^{19}F$ n.m.r. signals (CDCl$_3$) at $\phi*-55.3$ (t, $J_{HF}=27$ Hz, $—CH_2NF_2$). The mass spectrum had a molecular ion at m/e 173 [Accurate mass: M(173)=173.0653; calc. for $C_8H_9NF_2O=173.0652$].

EXAMPLE 5

1-Difluoroaminoadamantane (a) α-(Adamant-1-ylimino)toluene (835 mg., 3.5 mmole) dissolved in 50 c.c of chloroform at −20° C. was fluorinated using trifluoromethyl hypofluorite gas (ca. 8.5 mmoles) diluted with an approximately equal volume of nitrogen. The chloroform solvent contained about 0.75% v/v of ethanol as stabiliser so that the mole ratio of ethanol to imino compound in the reaction system was about 1.9:1. The hypofluorite gas was added over about 1 hour and the resulting solution allowed to stand with stirring for a further 2 hours at −20°. The solution was then warmed to room temperature, washed with ice-cold aqueous sodium bicarbonate and with water and was dried over magnesium sulphate. The solvent was distilled off and the residue chromatographed on an alumina column using n-hexane as eluant to give 1-difluoroaminoadamantane (455 mg., 71%). After sublimation at 100° and 20 mm. Hg pressure the product had m.p. 113°–115° (sealed tube) and exhibited $^1H$ and $^{19}F$ n.m.r. spectra identical to the product of Example 1(a).

(b) Similar results were obtained when the reaction was repeated using methylene chloride containing 1–2% v/v ethanol as solvent.

EXAMPLE 6

1-Difluoroaminoadamantane (a) α-(Adamant-1-ylimino)-p-methoxytoluene (540 mg., 2 mmole) dissolved in chloroform (25 c.c.) at −20° was fluorinated using trifluoromethyl hypofluorite gas (ca. 5 mmole) diluted with an approximately equal volume of nitrogen, and the product worked up as in Example 5 to give 1-difluoroaminoadamantane (206 mg., 55%) which after sublimation at 100° and 20 mm. Hg pressure had m.p. 113°–115° (sealed tube) and $^1H$ and $^{19}F$ n.m.r. spectra identical to the product of Example 1(a).

(b) Similar results were obtained using molecular fluorine in place of trifluoromethyl hypofluorite, the ratio of $N_2$:$F_2$ being about 5:1.

EXAMPLE 7

FLuorination of α-ethoxy-α-imino-p-fluorotoluene

α-Ethoxy-α-imino-p-fluorotoluene (335 mg., 2 mmoles) in a mixture of methylene chloride (5 c.c.) and trichlorofluoromethane (10 c.c.) containing 1 g. calcium oxide at −22° C. (carbon tetrachloride/dry ice bath) was fluorinated with a slight excess (ca. 2.1 mmoles) of trifluoromethyl hypofluorite gas diluted with an approximately equal volume of nitrogen. The reaction was monitored by GLC [3% HIEFF-8BP (cyclohexanedimethanol succinate) by weight on 100/120 Mesh Gas-Chrom Q in a 12 ft. glass column. Temperature=160° C. Nitrogen flow rate=35 c.c./min.]. Two peaks [retention times 2.7 (small peak) and 3.6 min.] of relative area 1:10 were observed. The starting material had retention time 3.3 min. The calcium oxide was filtered off, the solvent removed giving a slightly yellow liquid (360 mg.). Column chromatography over alumina (grade 3) eluting with n-hexane separated anti-α-ethoxy-α-fluorimino-p-fluorotoluene (A) (ca. 70%)

and syn-α-ethoxy-α-fluorimino-p-fluorotoluene (B) (ca. 8%).

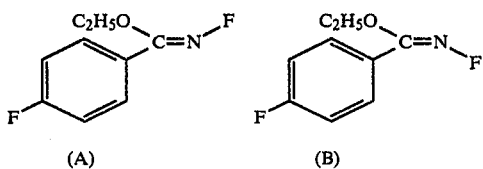

The anti-isomer had IR absorptions (liq. film) at 3000 (m), 1610(s, C═N), 1600(s), 1510(m), 1305(s), 1225(s), 1075(s), 1050(s), 1000(s), 870(s), 835(s), and 730(m). The $^1$H NMR spectrum (CCl$_4$) exhibited resonances at δ 1.4 (3H, dt, J=7 and 1 Hz), δ 4.6 (2H, dq, J=7 and 3 Hz), δ 7.0 (2H, m, aromatic protons), δ 7.7 (2H, m, aromatic protons). It had $^{19}$F resonances at $\phi^*+43.7$ (1F, s,—NF), $\phi^*+108.4$ (1F, m, aromatic fluorine) and UV absorption at $\lambda_{max}^{MeOH}=232$ (ε 8700). The mass spectrum had a molecular ion at m/e 185 (C$_9$H$_9$NF$_2$O+). (Found: C, 58.46; H, 5.01; N, 7.50; F, 20.68. C$_9$H$_9$NF$_2$O requires C, 58.57; H, 4.88; N, 7.53; F, 20.43%).

The syn-isomer had IR (liquid film) bands at 3000(m), 1610(s, C═N), 1510(s), 1320(s), 1280(s), 1240(s), 1020(s), 940(s), 850(s), and 785(s). The $^1$H NMR (CCl$_4$) spectrum displayed signals at δ 1.4 (3H, t, J=7 Hz, —OCH$_2$CH$_3$), δ 4.3 (2H, q, J=7 Hz, —OCH$_2$CH$_3$), δ 7.1 (2H, m, aromatic protons), δ 7.8 (2H, m, aromatic protons). $^{19}$F NMR (CDCl$_4$) $\phi^*+51.7$ (1F, s,—NF) and $\phi^*+107.8$ (1F, m, aromatic fluorine), UV $\lambda_{max}^{MeOH}=227$ (ε 7910). Its mass spectrum had a molecular ion at m/e 185 [Accurate mass: M(185)=185.0651; calc. for C$_9$H$_9$NF$_2$O=185.0652].

EXAMPLE 8

Fluorination of Schiff's bases derived from p-carboxybenzaldehyde (a) Powdered sodium hydroxide (1.2 mmole) was dissolved in methanol (20 ml) and p-carboxybenzaldehyde (1 mmole) was added. Adamantamine (1 mmole) was added and the resulting solution was stirred at room temperature for 24 hours. Potassium acetate (ca. 8 mmole) was added and the mixture was diluted with methylene chloride (25 ml) and was treated with trifluoromethyl hypofluorite (ca. 2.2 mmole) introduced by means of a vacuum line. The reaction mixture was maintained at room temperature for 2 hours, after which time the reaction was complete. The reaction mixture was then diluted with methylene chloride and water, and the organic layer was separated, washed with dilute aqueous sodium bicarbonate and treated with a small amount of deactivated neutral alumina. Filtration afforded 1-difluoroaminoadamantane identical with the product of Example 1(a).

(b) Similarly prepared were (+)- and (−)-1-phenyl-2-difluoroaminopropane (i.e. (+)- and (−)-difluoroamphetamine), identical with the products of Example 2; 2,4-dinitro-N,N-difluoroaniline, identical with an authentic sample; and 3-difluoroamino-3-deoxy-1,2:5,6-di-O-isopropylidene-α-D-allofuranose, the $^{19}$F n.m.r. spectrum of which showed the AB part of the expected ABX system as an eight line signal centred at $\phi^*-55$. In each case the starting material was the appropriate primary amine and replaced the adamantamine in (a) above.

EXAMPLE 9

Fluorination of N-benzylidene imine of 3-amino-3-deoxy-1,2:5,6-di-O-isopropylidene-α-D-allofuranose The imine (175 mg., 0.5 mmole) was dissolved in a mixture of methanol (5 ml) and methylene chloride (15 ml) and was treated at −20° with trifluoromethyl hypofluorite (~1.1 mmole) diluted with an approximately equal volume of nitrogen. After addition of the hypofluorite the solution was allowed to stand for 2 hours at −20°, with stirring, and was then warmed to room temperature, washed with dilute aqueous sodium bicarbonate and with water and was dried over magnesium sulphate. Evaporation of the solvent afforded a pale yellow oil, which was identified by $^1$H and $^{19}$F n.m.r. spectra as a mixture of 3-difluoroamino-3-deoxy-1,2:5,6-di-O-isopropylidene-α-D-allofuranose (the $^{19}$-F n.m.r. spectrum was essentially identical to that of the corresponding product in Example 3 (b)) and benzaldehyde dimethylacetal.

EXAMPLE 10

Fluorination of N-benzylidene imine of 2-amino-2-deoxyglucose-1,3,4,6-tetraacetate The imine (435 mg., 1.0 mmole) was dissolved in a mixture of dichloromethane (15 ml) and methanol (5 ml) and calcium oxide (250 mg) was added. The resulting solution was treated at room temperature with trifluoromethyl hypofluorite (2.5 mmole) applied using a vacuum line, and the solution was then allowed to stand at room temperature for 2 hours, with stirring. Thereafter the solution was washed with dilute aqueous sodium bicarbonate and with water and was dried over magnesium sulphate. Evaporation of the solvent afforded a pale yellow oil shown by $^1$H and $^{19}$F n.m.r. spectra to contain 2-difluoroamino-2-deoxyglucose-1,3,4,6-tetraacetate [$^1$H n.m.r. signals δ 6.1 (1H,d,J7.5 Hz, C-1H), δ 2.1 (3H,s, - Ac), δ 2.0 (9H,broad s, 3X-oAc) and $^{19}$F n.m.r. signals at $\phi^*-37$ (four line multiplet; probably centre portion of AB part of ABX system expected for >CHx-NF$_A$F$_B$) and $\phi^*+45$ (singlet)]; together with benzaldehyde dimethylacetal [$^1$H n.m.r. signals at δ 8.3 (s, —OMe), δ 5.3 (s,>CH-Ph) and δ 7.4 (m, Ph H)].

Preparation of starting materials

A—Preparation of imino ethers

The imino ethers used as starting materials in Examples 1–3 were prepared from the appropriate carboxamides by reaction with triethyloxonium fluoroborate, the carboxamides having been prepared in conventional manner from the appropriate amines and acid chlorides by the Schotten-Baumann reaction. The imino ethers were generally purified by distillation at reduced pressure, since chromatography on silica gel or alumina tended to result in partial or complete hydrolysis.

A(i)—Preparation of N-alkyl-p-fluorobenzamides and N-alkylbenzamides (a) p-Fluorobenzoyl chloride (or benzoyl chloride) (one equivalent) was shaken with primary alkylamine (one equivalent) suspended in 10 N potassium hydroxide until the smell of the acid chloride disappeared. The solid was filtered off, washed thoroughly with water and then dissolved in chloroform. The chloroform solution was then washed thoroughly with 2 N hydrochloric acid, saturated aqueous sodium bicarbonate, water, and dried over magnesium sulphate. Removal of the solvent gave the required amide in reasonable pure state. Analytical specimens were prepared by recrystallization from a mixture of chloroform and n-hexane.

(b) p-Fluorobenzoyl chloride (or benzoyl chloride) (one equivalent) was added slowly to a solution of the amine (one equivalent) in pyridine. The mixture was kept at room temperature overnight. The solution was then poured onto ice water and the solid was collected by filtration. The analytical sample was prepared as described above.

The following amides were prepared by one of the above procedures.

N-(1-Adamantyl)-p-fluorobenzamide had m.p. 163°–4° (Found: C, 74.55; N, 7.31; N, 4.90; F, 7.04. $C_{17}H_{20}NFO$ requires C, 74.70; H, 7.38; N, 5.12; F, 95%).

(+)-N-(1-Phenylisopropyl)-benzamide had m.p. 155°–6°, $\alpha_D^{23°} = +10.9°$ (c=36.8 mg./c.c.). (Found: C, 80.22; H, 7.10; N, 5.92. $C_{16}H_{17}NO$ requires C, 80.30; H, 7.14; N, 5.85%).

(−)-N-(1-Phenylisopropyl)-p-fluorobenzamide had m.p. 129°–30°, $\alpha_D^{23} = -13.8°$ (c=19.5 mg./c.c.). (Found: C, 74.61; H, 6.38; N, 5.27; F, 7.42. $C_{16}H_{16}FNO$ requires C, 74.68; H, 6.27; N, 5.44; F, 7.38%).

N-Stearylbenzamide had m.p. 87° (Found: C, 80.26; H, 11.52; N, 3.92. $C_{25}H_{43}NO$ requires C, 80.37; H, 11.60; N, 3.75%).

O,N-Dibenzoyltyramine had m.p. 172° (Found: C, 76.50; H, 5.65; N, 4.07. $C_{22}H_{19}NO_3$ requires C, 76.50; N, 5.55; N, 4.06%).

The above amides all had the expected IR and $^1H$ NMR spectra.

A (ii)—Preparation of Imino Ethers

A mixture of the amide (one equivalent) and triethyloxonium fluoroborate (slightly more than one equivalent) in dry methylene chloride was kept at room temperature overnight. The mixture was then washed with ice cold aqueous sodium carbonate, water, and dried over anhydrous magnesium sulphate. After the removal of methylene chloride, n-hexane was added to the residue to dissolve the imino ether. The solid (unreacted starting material) was filtered off, the filtrate then being distilled to give the imino ether. The following imino ethers were prepared by the above procedure.

α-Adamant-1-ylimino-α-ethoxy-p-fluorotoluene had m.p. 70°–71° (Found: C, 75.71; H, 8.03; N, 4.65; F, 6.30. $C_{19}H_{24}NFO$ requires C, 75.69; H, 8.11; N, 4.85; F, 6.48%).

(−)-α-(1-Phenylprop-2-ylimino)-α-ethoxytoluene had b.p. 128°–9°/0.2 mm. Hg, $n_D^{25°} = 1.5380$, $\alpha_D^{24°} = -48.1°$ (c=99 mg./c.c.). (Found: C, 80.81; H, 7.81; N, 5.30. $C_{18}H_{21}NO$ requires C, 80.86; H, 7.92; N, 5.24%).

(+)-α-(1-Phenylprop-2-ylimino)-α-ethoxy-p-fluorotoluene had b.p. 128°/0.2 mm. Hg, $n_D^{25°} = 1.5254$, $\alpha_D^{23°} = +47.4°$ (c=69.6 mg./c.c.). (Found: C, 75.62; H, 7.22; N, 5.01; F, 6.83. $C_{18}H_{20}NFO$ requires C, 75.76; H, 7.07; N, 4.91; F, 6.66%).

α-Ethoxy-α-stearyliminotoluene had IR absorptions (liq. film) at 2900 (vs), 1660(s, C=N), 1450(s), 1260(vs), 1110(s), 775(s), 700(s), and $^1H$ NMR resonances (CDCl$_3$) at δ 0.9–1.3 (38H), δ 3.4(2H, —CH$_2$N—), δ 4.3(2H, q, J=7 Hz, OC$\underline{H}_2$CH$_3$), δ 7.4(5H, aromatic protons).

B—Preparation of Schiff's bases

The Schiff's bases used as starting materials in Examples 5 and 6 were prepared by condensing the appropriate amines and aldehydes. Thus the amine (1 equivalent) in methanol solution may be added dropwise to a methanolic solution of the aldehyde and the solution allowed to stand at room temperature for 5–10 minutes. The Schiff's base is precipitated by the addition of water and may be crystallised from, for example, methanol. The following Schiff's bases were prepared in this way:

α-(Adamant-1-ylimino)toluene (from adamant-1-ylamine and benzaldehyde).

α-(Adamant-1-ylimino)-p-methoxytoluene (from adamant-1-ylamine and anisaldehyde); m.p. 104.5°–105.5°; $^1H$ n.m.r. (CDCl$_3$) δ 8.2 (1H, s, —N=C$\underline{H}$); δ 7.7 and δ 6.9 (4H, aromatic protons); δ 3.8 (3H, s, —OC$\underline{H}_3$) and δ 1.7–2.2 (15H, m, adamantyl protons).

C—Preparation of sugar amine derivatives

The sugar amine used as starting material in Example 8 (b) was prepared by reacting the corresponding allofuranose 3-tosylate with sodium azide in hexamethylphosphoramide to yield the 3-azide, which was reduced with lithium aluminium hydride in ether to afford the desired 3-amine. Treatment of the 3-amine with benzaldehyde in methanol gave the imine starting material for Example 9. The starting material for Example 10 was prepared by an analagous reaction sequence from the appropriate glucose 2-tosylate.

We claim:

1. A process for the preparation of an N,N-difluoroamine of the formula $$R-NF_2 \qquad \text{I}$$

where R represents a hydrogen atom or an organic group, comprising reacting a compound of the formula $$R^2-\overset{\overset{\displaystyle R^1}{|}}{C}=N-R \qquad \text{II}$$

where R is as defined for formula I, $R^1$ represents an organic group and $R^2$ represents a hydrogen atom or an organic group with a fluorinating agent selected from the group consisting of elemental fluorine and hypofluorites in which the fluoroxy group is bonded to an inert electron attracting group; with the proviso that if neither $R^1$ nor $R^2$ is a group capable of releasing electrons the reaction is effected in the presence of a nucleophilic compound.

2. A process as claimed in claim 1 wherein at least one of $R^1$ and $R^2$ is an electron-releasing organic group.

3. A process as claimed in claim 2 wherein the compound of formula II is a compound of the formula:

$$R^a-\overset{\overset{\displaystyle OR^b}{|}}{C}=N-R \qquad \text{III}$$

wherein R, $R^a$ and $R^b$ are alkyl containing 1 to 30 carbon atoms, monocyclic or polycyclic cycloalkyl groups containing 3 to 30 carbon atoms, sugar groups, steroidal groups, phenylalkyl groups containing 1 to 10 carbon atoms in the alkyl chain, aryl groups, and the above groups substituted by oxo, nitro, cyano, halo, carboxy, hydroxy, esterified hydroxy, sulphonyl, lower alkoxy, aralkoxy, aryloxy; $R^b$ may be a hydrocarbyl esterifying group possessing an oxo substituent in the 1-position.

4. A process as claimed in claim 2 wherein the starting material (II) is a compound of the formula:

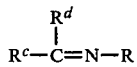

wherein R is alkyl containing 1 to 30 carbon atoms, monocyclic or polycyclic cycloalkyl containing 3 to 30 carbon atoms, sugar groups, steroidal groups; phenylalkyl groups containing 1 to 10 carbon atoms in the alkyl chain, aryl groups and the above groups substituted by oxo, nitro, cyano, halo, carboxy, hydroxy, esterified hydroxy, sulphonyl, lower alkoxy, aralkoxy or aryloxy; $R^c$ is hydrogen or alkyl containing 1 to 30 carbon atoms, monocyclic or polycyclic cycloalkyl containing 3 to 30 carbon atoms, sugar groups, steroidal groups; phenylalkyl groups containing 1 to 10 carbon atoms in the alkyl chain, aryl groups and the above groups substituted by oxo, nitro, cyano, halo, carboxy, hydroxy, esterified hydroxy, sulphonyl, lower alkoxy, aralkoxy or aryloxy; and $R^d$ is an electron releasing aromatic group comprising an aromatic ring carrying at least one electron-releasing substituent.

5. A process as claimed in claim 1 wherein organic groups R, $R^1$ and $R^2$ are each selected from $C_{1-20}$ alkyl groups, $C_{3-30}$ cyclo-aliphatic groups, aralkyl groups containing 1–10 carbon atoms in the alkyl chain, aryl groups and substituted versions of any of the said groups.

6. A process as claimed in claim 1 wherein said organic groups are selected from methyl, ethyl, propyl, butyl, hexyl, decyl, pentadecyl, heptadecyl, octadecyl, eicosyl, cyclopentyl, cyclohexyl, adamantyl, norbornyl, allose and glucose groups, benzyl, phenethyl, phenylpropyl, phenylisopropyl, phenyl, naphthyl and any of the said groups substituted by one or more of oxo, nitro, cyano, halo, carboxy, hydroxy, esterified hydroxy, sulphenyl, lower alkoxy, aralkoxy or aryloxy.

7. A process as claimed in claim 1 wherein the reaction is effected in the presence of a nucleophilic compound.

8. A process as claimed in claim 7 wherein the starting material is a compound of the formula:

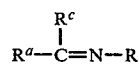
V wherein R and $R^a$ are alkyl containing 1 to 30 carbon atoms, monocyclic or polycyclic cycloalkyl groups containing 3 to 30 carbon atoms, sugar groups, steroidal groups, phenylalkyl groups containing 1 to 10 carbon atoms, in the alkyl chain, aryl groups and the above groups substituted by oxo, nitro, cyano, halo, carboxy, hydroxy, esterified hydroxy, sulphonyl, lower alkyl, aralkoxy or aryloxy; $R^c$ is hydrogen, alkyl containing 1 to 30 carbon atoms, monocyclic or polycyclic cycloalkyl groups containing 3 to 30 carbon atoms, sugar groups, steroidal groups; phenylalkyl groups containing 1 to 10 carbon atoms in the alkyl chain, aryl groups and the above groups substituted by oxo, nitro, cyano, halo, carboxy, hydroxy, esterified hydroxy, sulphonyl, lower alkoxy, aralkoxy or aryloxy.

9. A process as claimed in claim 1 wherein the fluorinating agent is a lower fluoroalkyl hypofluorite in which the fluoroalkyl group contains at least 2 fluorine atoms per carbon atom.

10. A process as claimed in claim 1 wherein the fluorinating agent is selected from the group consisting of trifluoromethyl hypofluorite and elemental fluorine diluted with an inert gas.

11. A process as claimed in claim 1 wherein the fluorinating agent is a gaseous or volatile liquid hypofluorite and the reaction is conducted in a polar organic solvent selected from the group consisting of methylene dichloride, chloroform, chlorotrifluoromethane, acetone, diethyl ether and tetrahydrofuran.

12. A process for the preparation of an N-monofluoroamine of formula

RNHF 

where R is as defined in claim 7 wherein a compound of formula II as defined in claim 1 is reacted with about one equivalent of a fluorinating agent as defined in claim 1 and the reaction product is hydrolysed to yield the desired N-monofluoroamine (VI) or a salt thereof.

13. A process as claimed in claim 1 in which (−)-α-(1-phenylprop-2-ylimino)-α-ethoxytoluene is reacted with trifluoromethyl hypofluorite gas to prepare (+)-1-phenyl-2-difluoroaminopropane.

14. The process of claim 3 wherein R, $R^a$ and $R^b$ are methyl, ethyl, propyl, butyl, hexyl, decyl, pentadecyl, heptadecyl, octadecyl, eicosyl; cyclopentyl, cyclohexyl, adamantyl or norbornyl, allose, glucose, benzyl, phenethyl, phenylpropyl or phenylisopropyl; phenyl, naphthyl; and the above groups substituted by oxo, nitro, cyano, fluoro or chloro, carboxy, hydroxy, acetoxy, propionoxy, benzoyloxy, benzenesulphonyl, methoxy, ethoxy, benzyloxy or phenoxy.

15. The process of claim 4 wherein R is methyl, ethyl, propyl, butyl, hexyl, decyl, pentadecyl, heptadecyl, octadecyl, eicosyl; cyclopentyl, cyclohexyl, adamantyl or norbornyl, allose, glucose, benzyl, phenethyl, phenylpropyl or phenylisopropyl, phenyl, naphthyl, and the above groups substituted by oxo, nitro, cyano, fluoro or chloro, carboxy, hydroxy, acetoxy, propionoxy, benzoyloxy, benzenesulphonyl, methoxy, ethoxy, benzyloxy, phenoxy; $R^c$ is hydrogen or R as defined, and $R^d$ is phenyl substituted in the ortho, para or ortho and para positions with methoxy, ethoxy, n-propoxy, isopropoxy, t-butoxy; benzyloxy, phenoxy; sulphur analogues of said oxygen functions; and dialkylamino wherein the alkyl group contains 1 to 6 carbon atoms.

16. The process of claim 8 wherein R, $R^a$ and $R^c$ are methyl, ethyl, propyl, butyl, hexyl, decyl, pentadecyl, heptadecyl, octadecyl, eicosyl; cyclopentyl, cyclohexyl, adamantyl or norbornyl, allose, glucose, benzyl, phenethyl, phenylpropyl or phenylisopropyl, phenyl, naphthyl; and the above groups substituted by oxo, nitro, cyano, fluoro or chloro, carboxy, hydroxy, acetoxy, propionoxy, benzoyloxy, benzenesulphonyl, methoxy, ethoxy, benzyloxy or phenoxy.

17. The process of claim 3 wherein $R^b$ is $C_{1-20}$ alkyl, $R^a$ is phenyl and R is phenylalkyl containing 1 to 10 carbon atoms in the alkyl chain.

18. The process of claim 1 wherein the nucleophilic compound is an alcohol or salt of an organic carboxylic acid.

19. The process as claimed in claim 4 wherein $R^d$ is phenyl substituted in the ortho, para or ortho and para positions by a $C_{1-6}$ alkoxy group, aryl $C_{1-6}$ alkoxy, phenoxy, $C_{1-6}$ alkylthio, aryl $C_{1-6}$ alkylthio, phenylthio or di-$C_{1-6}$ alkylamino group.

20. A process as claimed in claim 18 wherein said nucleophilic compound comprises methanol or ethanol.

* * * * *